United States Patent [19]

Kuroishi et al.

[11] Patent Number: 4,582,687
[45] Date of Patent: Apr. 15, 1986

[54] APPARATUS FOR FLOW ANALYSIS

[75] Inventors: Tadafumi Kuroishi; Hideo Uchiki, both of Katsuta, Japan

[73] Assignee: Hitachi, Ltd., Tokyo, Japan

[21] Appl. No.: 396,881

[22] Filed: Jul. 9, 1982

[30] Foreign Application Priority Data

Jul. 13, 1981 [JP] Japan .................... 56-108268

[51] Int. Cl.[4] .............. G01N 35/08; G01N 21/05
[52] U.S. Cl. ............................ 422/82; 356/410; 436/53
[58] Field of Search .......... 250/573, 576; 356/410, 356/411, 328; 422/68, 81, 82, 93, 64, 65, 67; 436/43, 50, 52, 53, 34

[56] References Cited

U.S. PATENT DOCUMENTS

| | | | |
|---|---|---|---|
| 2,152,973 | 4/1939 | Rathwell | 250/573 X |
| 3,074,784 | 1/1963 | Ferrari | 422/70 |
| 3,230,048 | 1/1966 | Skeggs | 422/70 |
| 3,784,310 | 1/1974 | Barton et al. | 436/53 X |
| 3,804,593 | 4/1974 | Smythe et al. | 436/53 |
| 3,921,439 | 11/1975 | Burns | 422/82 X |
| 3,999,861 | 12/1976 | Bellinger | 356/410 |
| 4,022,575 | 5/1977 | Hansen et al. | |
| 4,102,177 | 7/1978 | Okada et al. | 73/32 R |
| 4,263,512 | 4/1981 | Sagusa et al. | 356/407 X |
| 4,338,279 | 7/1982 | Orimo et al. | 422/67 X |

FOREIGN PATENT DOCUMENTS

| | | | |
|---|---|---|---|
| 52-62488 | 5/1977 | Japan | 356/410 |
| 1315603 | 5/1973 | United Kingdom . | |

Primary Examiner—Barry S. Richman
Assistant Examiner—Michael S. Gzybowski
Attorney, Agent, or Firm—Antonelli, Terry & Wands

[57] ABSTRACT

Apparatus in which a sample and a reagent solution are introduced into a stream of carrier liquid, whereby reaction proceeds between the sample and the reagent solution during their transfer through a passage. When a zone of the reaction solution passes successively through two flow cells provided in series, light absorbancy based on the reaction solution in each flow cell is measured, and rate assay is made from a difference between light absorbancies. A period of time for observing a specific sample can be changed by changing the length of a reaction tube connecting a flow cell at the upstream side to a flow cell at the downstream side.

26 Claims, 4 Drawing Figures

APPARATUS FOR FLOW ANALYSIS

BACKGROUND OF THE INVENTION

This invention relates to a method and an apparatus for flow analysis, and particularly to a method and an apparatus suitable for rate assay.

A method comprising providing a flow cell in a carrier liquid passage, introducing a sample and a reagent solution into a stream of a carrier liquid, and observing a state of reaction therebetween by a photometer is known as flow analysis, whose specific structure is disclosed in U.S. Pat. No. 4,022,575, where a reaction solution of a sample and a reagent is introduced into a single flow cell through a reaction coil and thus colorimetric analysis is carried out continuously and efficiently by successively introducing samples into the passage.

The conventional flow analyzer is suitable for end point assay, and not suitable for rate assay. Rate assay by the conventional flow analyzer is poor in analytical treatment efficiency, because, if a zone of a reaction solution of a sample and a reagent solution enters into a flow cell, solution transfer must be stopped for the necessary time for observation.

SUMMARY OF THE INVENTION

An object of the present invention is to provide a method and an apparatus for rate assay without retaining a reaction solution in a flow cell for a long time, that is, a method and an apparatus for efficient analysis.

Another object of the present invention is to provide a method and an apparatus capable of readily meeting changes in reaction time for one sample to another for observation.

According to the present invention, a plurality of flow cells are provided in a light path of a photometer, and are connected to one after another through reaction tubes. When a zone of a reaction solution of a sample and a reagent solution, as introduced into the flow passage, enters into a first flow cell, a first light absorbancy is measured, and then, when the zone of the reaction solution enters into a second flow cell, a second light absorbancy is measured. Reaction rate of a given analytical item is determined from the difference between the first and second light absorbancies. Reaction tubes having various lengths are made ready for the connection between the flow cells, and a reaction tube having an appropriate length is selected in view of the necessary time for observation.

DESCRIPTION OF THE PREFERRED EMBODIMENTS

Figure 1:
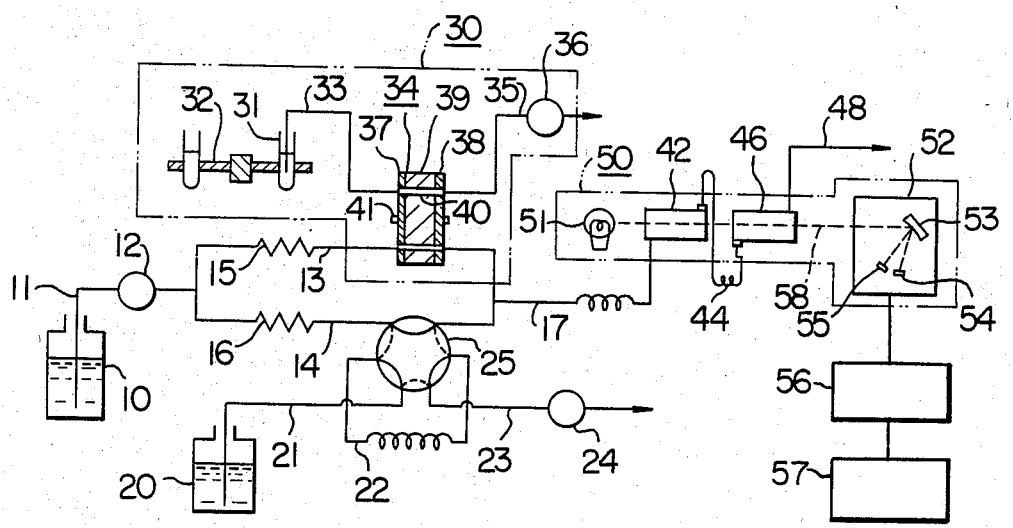
FIG. 1 is a flow diagram showing an arrangement according to one embodiment of the present invention.

In FIG. 1, a carrier liquid, which is distilled water, is placed in reservoir 10, and is taken into suction tube 11 by suction, and led to flow passages 13 and 14 by transfer pump 12, which is a peristaltic pump. The carrier liquids, which have passed through passages 13 and 14, are joined together in passage 17, and passed through flow cell 42, reaction tube 44, flow cell 46 and passage 48, and then discharged. Passage resistances 15 and 16 are adjusted according to a flow rate proportion of passage 13 to passage 14.

Passage 13 extends through metering perforation 40 of rotary switch valve 34. Sample 30 is provided for introducing a predetermined volume of a sample into the carrier liquid stream in passage 13. A plurality of sample cups 31 each containing a sample is provided on turn table 32. When a given sample cup 31 is positioned at a suction point, suction tube 33 is inserted into sample cup, and a sample is taken into rotary switch valve 34 by suction generated by working of transfer pump 36. When the sample fills the metering perforation of switch valve 34, working of transfer pump 36 is discontinued. Rotary switch valve 34 is comprised of fixed members 37 and 38 and rotary member 39. Rotary member 39 has a large number of metering perforations 40, each having a volume of 10 $\mu$l. When rotary member 39 turns by one step around shaft 41, the next metering perforation is communicated with suction tube 33. Turn table 32 advances by one step, and another sample in the next sample cup is introduced into the metering perforation communicated with suction tube 33 therethrough. When metering perforation 40 containing the sample is communicated with passage 13, the sample is transferred by the carrier liquid stream.

On the other hand, passage 14 extends through 6-way switch valve 25. When transfer pump 24 works, a reagent solution for measuring GOT (glutamate oxalate transaminase) in reservoir 20 is taken into passage 23 through passage 21 and metering tube 22. When the reagent solution fills metering tube 22 having a capacity of 200 $\mu$l, the working of transfer pump 24 is discontinued. Then, six-way switch valve 25 is switched as shown by dotted lines in FIG. 1, and the carrier fluid pushes the reagent solution from metering tube 22 into passage 17.

A zone of the sample sandwiched between the carrier liquids from passage 13 and a zone of the reagent solution sandwiched between the carrier liquids from passage 14 are joined together in passage 17 to form a zone of reaction solution. The reaction solution gradually undergoes reaction while it passes through the passage.

Figure 2:
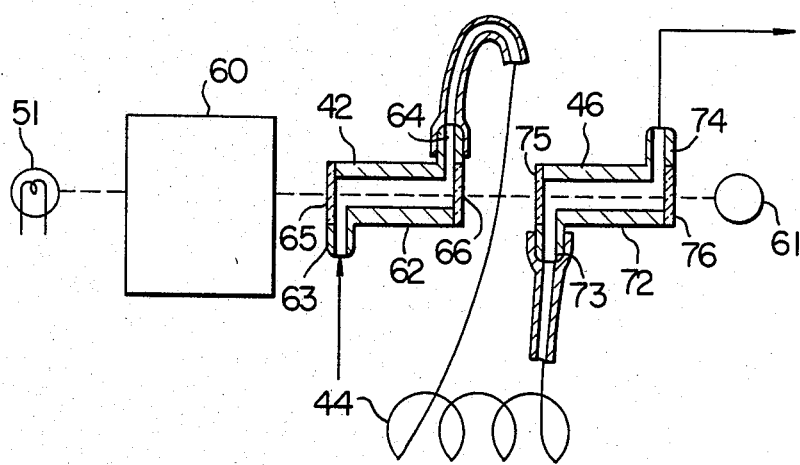
FIG. 2 is a schematic arrangement of a photometer and members relating to it according to another embodiment of the present invention.

Flow cells 42 and 46 have the same structure as shown in FIG. 2. Flow cells 42 and 46 in FIG. 1 are within photometer 50 and arranged in series to light path 58. White light from light source 51 irradiates flow cell 42, and the light transmitted through flow cell 42 irradiates flow cell 46. The light transmitted through flow cell 46 enters into spectrometer 52, in which concave refractive lattice 53 and a large number of photoelectric detectors 54 and 55 are provided. Detector 54 is arranged at a position corresponding to the position of wavelength absorbed by a given analytical item, and detector 55 is arranged at a position corresponding to the position of wavelength not absorbed by the analytical item, and thus light measurement of dual wavelength is carried out by comparing and computing two signals of wavelength by computer section 56. A microcomputer provided in computer section 56 controls functioning of transfer pumps, turn table 32, rotary switch valve 34, six-way switch valve 25 and a multiplexer of taking out light signals of dual wavelength.

Results of computation are displayed on display section 57 with CRT and a printer.

In FIG. 1, spectrometer 52 of photometer 50 is provided after the series of flow cells, but it can be provided before flow cells, as photometer 60 shown in FIG. 2. According to the structure of FIG. 2, a dispersing member is provided in spectrometer 60, where monochromatic light of single wavelength or dual wavelength irradiates flow cells. Flow cells 42 and 46 have the same shapes. Light transmission windows 65, 66, 75 and 76 of quartz are provided at both ends of flow cell bodies 62 and 72. Inlet 63 of flow cell 42 is connected to passage 73, and outlet 74 of flow cell 46 is connected to passage 48. End parts of reaction tube 44 are comprised of fluorine resin tube having a low elasticity. One end of reaction tube 44 is engaged with outlet 64 of flow cell 42, and other end thereof is engaged with inlet 73 of flow cell 46. The ends of reaction tube 44 are detachable by detachable fixing means. The monochromatic light transmitted through the flow cells is detected by detector 61.

While the zone of reaction solution formed in passage 17 of FIG. 1 stays in flow cell 42, a first light absorbancy based on the reaction solution is measured. Then, the zone of reaction solution flows through reaction tube 44 and enters into flow cell 46. During the transfer, reaction further proceeds between the sample and the reagent. While the zone of reaction solution stays in flow cell 46, a second light absorbancy based on the reaction solution is measured. Zones of other reaction solutions can be successively fed into the passage by synchronizing functions of sampler 30 and six-way switch valve 25.

Figure 4:
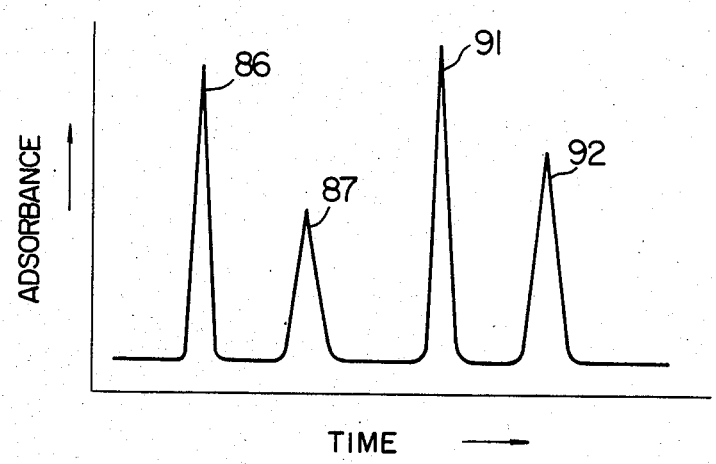
FIG. 4 is a diagram showing results of measurement according to the present invention.

In FIG. 4, results of measurement according to the present invention are shown, where two samples are successively passed by a carrier liquid stream to measure light absorbancies. Peak 86 shows a result of first measurement of a first sample, peak 87 a result of second measurement of the first sample, peak 91 a result of first measurement of a second sample, and peak 92 a result of second measurement of the second sample. The difference between peaks 86 and 87 and that between peaks 91 and 92 are changes due to the progress of reaction. Since the reaction solution or liquid mixture diffuses into the carrier liquid while the reaction solution or liquid mixture is transferred through reaction tube 44, the zone of reaction solution is broader at the second measurement. In that case, the change can be corrected by determining the area of each peak.

Flow cells 42 and 46 each are 0.8 mm in inner diameter and 10 mm in path length, and reaction tube 44 is 0.5 mm in inner diameter and 200 cm in length.

In the embodiments of FIG. 1 and FIG. 2, passage 21 is inserted into another reagent reservoir, when GOT measurement of a series of samples on turn table 32 is completed. At that time, a reagent, for example, for GPT (glutamate pyruvate transaminase) is made ready as another reagent solution. At the same time, reaction tube 44 is replaced with another reaction tube with different length, whereby a suitable time interval between a first measurement and a second one for GPT observation can be selected.

Figure 3:
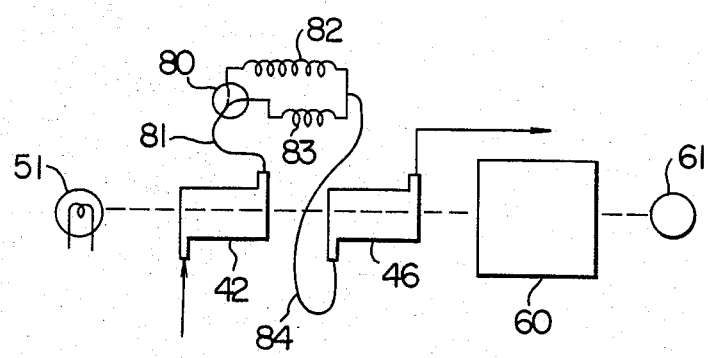
FIG. 3 is another schematic arrangement of a photometer and members relating to it according to further embodiment of the present invention.

In the embodiment of FIG. 3, spectrometer 60 is provided after a series of flow cells, and there is a mechanism of selecting the length of reaction tube between the outlet of flow cell 42 at the upstream side and the inlet of flow cell 46 at the downstream side. That is, passage 81, which is connected to the outlet of flow cell 42 at one end, is connected to switch valve 80 at another end. Passage 84, which is connected to the inlet of flow cell 46 at one end, is connected to long reaction tube 82 and short reaction tube 83 at another end. Three or more reaction tubes can be used.

According to the structure of FIG. 3, a time interval between a first measurement of light absorbancy and a second measurement of light absorbancy for observation can be readily selected in view of the kind of sample or difference in analytical items.

In the foregoing embodiments, two flow cells are provided, but three or more flow cells can be provided in series in the same light path of a photometer. In that case, number of observations is increased in accordance with the number of flow cells.

What is claimed is:

1. An apparatus for flow analysis, which comprises a photometer for providing a single light path, a plurality of flow cells provided in series in said single light path, each flow cell having an inlet and an outlet for flow therethrough and being positioned such that flow therethrough is substantially in the direction of said light path, reaction tube means connecting adjacent flow cells, said reaction tube means being connected at one end to the outlet of one of the flow cells and at another end to the inlet of an adjacent flow cell, said photometer including a light detector capable of detecting light transmitted through said plurality of flow cells, a means for transferring a reaction solution of a sample and a reagent solution from a flow cell at an upstream side to a flow cell at a downstream side through the reaction tube means, and means for introducing the reaction solution to the plurality of flow cells such that only one of said plurality of flow cells contains reaction solution when said light detector is detecting light, whereby said reaction solution can be analyzed in each of said plurality of flow cells using said single light path.

2. The apparatus according to claim 1, wherein said flow cells are provided at ends thereof with light transmission windows for transmission of light therethrough in the direction of said single light path.

3. The apparatus according to claim 1, wherein said light detector is capable of detecting light transmitted via said single light path through said plurality of flow cells.

4. The apparatus according to claim 1, further comprising means for introducing a predetermined amount of sample into a first stream of carrier liquid, means for introducing a predetermined amount of reagent solution into a second stream of carrier liquid, and means for combining the first and second streams of carrier fluid to form a zone of reaction solution sandwiched between segments of carrier liquid prior to introduction into the plurality of flow cells.

5. The apparatus according to claim 1, further comprising means for transporting said reaction solution to said plurality of flow cells, said means for transporting including means for passing said reaction solution to said plurality of flow cells in zones of reaction solution, sandwiched by separating fluid.

6. The apparatus according to claim 1, wherein said reaction tube means is detachably connected to said adjacent flow cells.

7. The apparatus according to claim 6, wherein the reaction tube means has a plurality of reaction tubes with different lengths, and a means for selectively, operatively connecting one of the reaction tubes for reaction solution flow therethrough.

8. An apparatus for flow analysis, which comprises a photometer for providing a single light path, a plurality of flow cells provided in flow communication from an upstream side to a downstream side and in series in said single light path, reaction tube means being detachably connected at one end to an outlet of a flow cell at the upstream side and at another end to an inlet of a another flow cell at the downstream side, said photometer having a light detector capable of detecting light transmitted through said plurality of flow cells, a means for transferring a reaction solution of a sample and a reagent from a flow cell at the upstream side to a flow cell at the downstream side through the reaction tube means, and means for introducing the reaction solution to the plurality of flow cells such that only one of said plurality of flow cells contains reaction solution when said light detector is detecting light, whereby said reaction solution can be analyzed in each of said plurality of flow cells using said single light path.

9. The apparatus according to claim 8, further comprising means for measuring light absorbancy every time when a zone of a reaction solution transferred in a passage in a sandwiched state by carrier liquids passes through each of the flow cells.

10. The apparatus according to claim 8, wherein the reaction tube means has a plurality of reaction tubes with different lengths, and a means for selectively, operatively connecting one of the reaction tubes for reaction solution flow therethrough.

11. The apparatus according to claim 8, wherein said light detector is capable of detecting light transmitted via said single light path through said plurality of flow cells.

12. The apparatus according to claim 8, further comprising means for introducing a predetermined amount of sample into a first stream of carrier liquid, means for introducing a predetermined amount of reagent solution into a second stream of carrier liquid, and means for combining the first and second streams of carrier fluid to form a zone of reaction solution sandwiched between segments of carrier liquid prior to introduction into the plurality of flow cells.

13. The apparatus according to claim 8, further comprising means for transporting said reaction solution to said plurality of flow cells, said means transporting including means for passing said reaction solution to said plurality of flow cells in zones of reaction solution, sandwiched by separating fluid.

14. An apparatus for flow analysis, which comprises a photometer for providing a single light path, a plurality of flow cells arranged in series and in said single light path, a reaction tube means connecting adjacent flow cells, said reaction tube means having one end detachably connected to an outlet of an upstream flow cell and another end that is detachably connected to an inlet of an adjacent downstream flow cell, said photometer having a light source capable of irradiating the plurality of flow cells, and a light detector capable of detecting light transmitted through the plurality of flow cells, means for providing a first measurement value while a zone of reaction solution is in the flow cell at the upstream side of a reaction tube means and for providing a second measurement value while the zone of reaction solution is in the flow cell at the downstream side of a reaction tube means, a passage means for transferring a carrier liquid, the passage means being provided at an upstream side of the plurality of flow cells, a means for introducing a predetermined amount of a sample and a predetermined amount of a reagent solution into the passage means, the sample and reagent solution combining to form reaction solution, and means for introducing the reaction solution to the plurality of flow cells such that only one of said plurality of flow cells contains reaction solution when said light detector is detecting light, whereby the zone of reaction solution can be analyzed in each of said plurality of flow cells using the single light path.

15. The apparatus according to claim 14, wherein the photometer has a spectrometer provided after said plurality of flow cells, and the spectrometer has a concave refractive lattice.

16. The apparatus according to claim 14, wherein the photometer measures a detection signal based on dual wavelengths.

17. The apparatus according to claim 14, wherein the reaction tube means has a plurality of reaction tubes with different lengths, and a means for selectively operatively connecting one of the reaction tubes for reaction solution flow therethrough.

18. The apparatus according to claim 14, wherein the means for introducing the sample and the reagent solution has a sampler capable of introducing a plurality of different samples successively into the passage means.

19. The apparatus according to claim 14, wherein said means for providing a first measurement value and for providing a second measurement value includes means for displaying the first and second measurement values.

20. The apparatus according to claim 14, wherein the photometer has a spectrometer provided before said plurality of flow cells.

21. The apparatus according to claim 14, wherein the light source is positioned to irradiate each of said plurality of flow cells in a direction along said light path, from an upstream side of each flow cell to a downstream side of said each flow cell.

22. The apparatus according to claim 14, wherein said means for providing a first measurement value and a second measurement value includes means for providing first and second measurement values derived from light detected by said light detector when said zone of reaction solution is in the flow cell at the upstream side of a reaction tube and from light detected by said light detector when said zone of reaction solution is in the flow cell at the downstream side of the reaction tube means, said light detected by said light detector being passed through the plurality of flow cells via said single light path.

23. The apparatus according to claim 14, wherein said light detector is capable of detecting light transmitted via said single light path through said plurality of flow cells.

24. The apparatus according to claim 14, further comprising means for combining the sample and the reagent solution to form the zone of reaction solution, and wherein said means for introducing is adapted to introduce said zone of reaction solution sandwiched between segments of carrier liquid.

25. The apparatus according to claim 14, wherein said means for introducing and said passage means, in combination, include means for a zone of reaction solution, sandwiched between zones of separating fluid, to said plurality of flow cells.

26. The apparatus according to claim 25, wherein said separating fluid is said carrier liquid.

* * * * *